United States Patent [19]

Fanselow et al.

[11] 4,130,760
[45] Dec. 19, 1978

[54] REUSABLE RADIATION MONITOR

[75] Inventors: Dan L. Fanselow, White Bear Lake; Dean A. Ersfeld, Maplewood, both of Minn.

[73] Assignee: Minnesota Mining and Manufacturing Company, Saint Paul, Minn.

[21] Appl. No.: 811,253

[22] Filed: Jun. 29, 1977

[51] Int. Cl.² .............................................. G01N 5/00
[52] U.S. Cl. .................................... 250/474; 548/346
[58] Field of Search ...................... 250/474; 548/346; 96/90 PC; 116/114 R

[56] References Cited
U.S. PATENT DOCUMENTS

| | | | |
|---|---|---|---|
| 3,609,165 | 9/1971 | Heine et al. | 548/324 |
| 3,710,109 | 1/1973 | Chalkley | 250/474 |
| 3,787,687 | 1/1974 | Trumble | 250/474 |

Primary Examiner—Davis L. Willis
Attorney, Agent, or Firm—Cruzan Alexander; Donald M. Sell; Carolyn A. Bates

[57] ABSTRACT

An integrating, reusable device for monitoring exposure to actinic radiation is disclosed. The device comprises a substrate having deposited thereon at least one photochromic aziridine compound which is sealed in an oxygen barrier to stabilize the color developed by the aziridine compound in response to actinic radiation. The device includes a spectral response shaping filter to transmit only actinic radiation of the type being monitored. A color standard is also provided with which to compare the color developed by the aziridine compound.

11 Claims, 5 Drawing Figures

REUSABLE RADIATION MONITOR

This invention relates to a photochemical process and device for monitoring exposure to actinic radiation, especially ultraviolet radiation. More particularly, the invention relates to a process and device by which exposure to actinic radiation can be monitored visually by comparing the color developed by a photochromic compound with a color standard representing a known level of radiation exposure.

Ultraviolet light monitors for use as sunburn warning devices are known in the art. For example, U.S. Pat. No. 3,903,423 describes a sunburn dosimeter utilizing a chemical compound which develops an irreversible color change in response to radiation in the sunburn region of about 290 to 320 nanometers. Adjacent to the test zone containing the photochromic compound is provided at least one color standard panel with which to compare the color developed by the photochromic compound. When the color developed by the test zone matches the color of the appropriate color standard, the user knows how much radiation in the sunburn region he or she has been exposed to.

U.S. Pat. No. 3,449,572 describes the use of solutions of triphenyltetrazolium chloride to sense ultraviolet radiation. The compound develops a dark red color when exposed to ultraviolet light. A sunburn dosimeter is described wherein the triphenyltetrazolium compound is coated on a substrate which is mounted adjacent to a color standard. A similar device is described in U.S. Pat. No. 3,194,963 using 2-(2',4'dinitrobenzyl)-pyridine as the light sensitive material. This device may include a number of structural features such as a filter system to reduce the amount of light reaching the pyridine compound.

One significant disadvantage associated with most monitoring devices of the prior art is that they are not reusable. Once the color of the photochromic material has developed, it is irreversible and the device must be discarded. It is generally considered undesirable to utilize photochromic materials which exhibit reversible color changes in monitoring devices. If the color change is reversible, the device can not integrate incident radiation and inaccurate monitoring may result. For this reason, stabilizers are often added to prevent the color developed by the photochromic material from fading.

The radiation monitoring device of the present invention utilizes certain photochromic aziridine compounds described in U.S. Pat. No. 3,609,165. These compounds are initially white or cream-colored crystals which are rapidly converted to blue when exposed to ultraviolet light or electron beam radiation. The color is reversible and fades rapidly when placed in the dark. The color developed by these compounds also fades when exposed to visible light and/or heat, (e.g., above 50° C.). Because the color change is reversible, these compounds do not suggest themselves as useful candidates for an integrating radiation monitoring device.

However, it has been discovered that sealing these aziridine compounds in an oxygen barrier will stabilize the color developed in response to ultraviolet light or electron beam radiation by minimizing fading in the dark or upon exposure to heat. It has been further discovered that the oxygen barrier does not prevent the color from being bleached by exposure to visible light free of ultraviolet radiation. These discoveries have been used to fashion an integrating radiation monitoring device which can be used for a variety of purposes, and has the desirable feature of being reusable.

According to the present invention there is provided an integrating, reusable device for monitoring actinic radiation of a preselected character comprising a substrate having deposited thereon at least one photochromic aziridine compound of the formula:

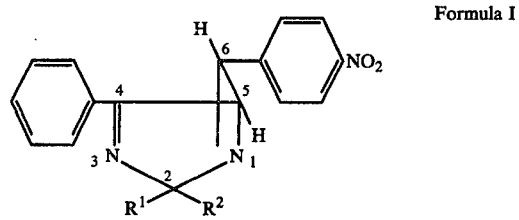

Formula I wherein $R^1$ and $R^2$ taken separately are hydrogen, alkyl having one to six carbon atoms inclusive, phenyl or ortho or para lower alkyl or lower alkoxy substituted phenyl, or where $R^1$ and $R^2$ taken together are alkylene having 4 to 7 carbon atoms inclusive. These compounds are synthesized by the method disclosed by Heine et al in J. Org. Chem. 32, 2708-10 (1967) and in U.S. 3,609,165.

The term "lower" as used herein to modify "alkyl" or "alkoxy" means alkyl or alkoxy groups having 1 to 4 carbon atoms, inclusive.

Associated with the aziridine compound is an oxygen barrier to substantially prevent contact of the aziridine compound with oxygen. The oxygen barrier must be chemically inert with respect to the aziridine compound and transparent or reasonably transmitting to the actinic radiation being monitored. Filter means are disposed between the aziridine compound and the source of actinic radiation to allow only radiation of the character being monitored to reach the aziridine compound. At least one color standard is provided with which to compare the color developed by the aziridine compound. In the preferred embodiment, the color standard is separate from the aziridine compound, e.g. as the background color of the substrate. When the color developed by the aziridine compound matches the appropriate color standard, the user is informed that the preselected amount of radiation exposure has been reached.

The amount of radiation causing the specific aziridine to develop the color of the color standard may be accurately determined by measuring the intensity of the lamp output with a photometer at the sample plane and the time of exposure. The product of the intensity and exposure time gives the exposure (e.g. joules/cm$^2$). The visual match between the color of the patch and the color standard is defined as the "end point." Several different patches of one specific aziridine may be used with a given reference color. Each patch may be covered by a different filter to attenuate the amount of radiation to which the aziridine compound is exposed. Then, each patch is calibrated so that a user will be informed as to the amount of radiation required to color match each patch with the reference color. Alternatively, a specific aziridine may be color matched with several different standards. Again, each color match will represent a different precalibrated exposure. However, it is preferable to use a single color standard.

Where more than one discrete patch of aziridine compound are present and the patches have different sensitivities to the actinic radiation being monitored (by overlaying the patches with attenuating layers of differing strengths), a separate color standard is not required. In such a monitor, the aziridine patches themselves can serve as a means of comparison to alert the user that the predetermined amount of radiation has been reached. Since optical density at saturation (deepest blue color possible) of each photochromic aziridine is relatively constant, a saturated patch may be used as a color standard for another unsaturated patch.

The patch with the filter which attenuates the least will reach saturation first, and the filter which attenuates the most will reach saturation last. Thus, with photometric calibration, the exposure for saturation may be determined for each patch. Hence, it is possible to use a monitor containing a series of patches, which encompass at some intermediate level a predetermined critical level of exposure. For example, if the permissible eight hours dose is 3.0 millijoules/cm$^2$, a monitor having patches which reach saturation at 1.0, 2.0, 3.0, 4.0 and 5.0 millijoules/cm$^2$ could be used. The user would note that the first patch colors and reaches saturation first, and then the second will follow suit. At this point, the user has been exposed to two millijoules/cm$^2$. The third patch is becoming blue and the fourth patch is lighter blue. Some time prior to the third patch becoming the same color as the first and second patches, the user should leave the actinic radiation area to avoid becoming exposed to the permissible limit.

The term "actinic radiation" as used herein refers to radiation which causes the photochromic aziridine compounds of Formula I to change from one form to another, e.g. the colorless to the colored form or the colored to the colorless form. Actinic radiation such as ultraviolet light or electron beam radiation will cause the aziridine compounds of Formula I to change to various shades of blue depending upon the R$^1$ and R$^2$ groups present. Visible light will cause the compounds to change from the blue form to colorless. The preferred compounds of Formula I for use in the monitor are those wherein R$^1$ and R$^2$ are CH$_3$ and those wherein R$^1$ + R$^2$ together are cyclohexyl or cyclopentyl.

The color developed by the photochromic compound can be bleached by exposure to visible radiation (free of ultraviolet radiation) such as a yellow "Bug Lite" or UV-blocked sunlight, and the monitor may be reused with little loss in accuracy.

The monitor of the present invention is especially useful in the treatment of psoriasis, where a patient receives a photoactive drug and is periodically exposed to ultraviolet radiation. An article by Parrish et al. in the New England Journal of Medicine 291, 1207–11 (1974) describes psoriasis photochemotherapy. The patient is first treated with a photoactive drug (e.g., 8-methoxypsoralen) by oral or topical administration, followed by exposure to specific actinic radiation. Generally, the near UV radiation in the range of 320 to 390 nanometers is utilized. The quantity of radiation required varies between about 1 and 20 joules/cm$^2$ and is dependent upon patient tolerance and response to the drug. The procedure is expected to involve an initial intensive treatment phase followed by a long term maintenance program. Each patient is initially "titrated" to determine tolerance and effectiveness of treatment. Since the amount of UV exposure utilized in the treatment is critical to both the efficacy of the photoactive drug and the minimization of toxic reactions such as erythema, an accurate monitoring of radiation exposure is important.

Currently, expensive electronic integrating devices are being utilized and developed to monitor the radiation dosage. The inexpensive, easily fabricated, reliable, accurate and reusable monitor of the present invention is well suited for use in this treatment method.

The monitor of the invention can also be utilized as a sun exposure monitor, although for this use it is desirable to add an additional filter to prevent color bleaching from the large amount of visible radiation present in sunlight. The device may be used by a sunbather or those concerned about sensitivity to the solar radiation, and the appropriate change in color of the aziridine compound indicates the amount of exposure to erythemal radiation. The monitor may also be used to indicate necessary adjustments for solar collector panels by comparing the rate of change of the color with panel position.

Since the photochromic aziridines used in this invention respond to actinic radiation as far out as about 450 nanometers; the device, with appropriate filters, may be used to monitor the exposure received by plant life. Cumulative light exposure around 435 nanometers (blue) is indicated by the change from colorless to blue, and alternatively exposure around 675 nanometers (red) can be correlated with the extent of optical bleaching from blue to colorless. Thus, light exposure which affects processes such as chlorophyll formation, photomorphogenesis, phototropism, etc. can be monitored.

The device may also be used to monitor ultraviolet therapy given to infants undergoing treatment for jaundice. Another use for the device is in monitoring exposure by industrial workers to ultraviolet light and electron beam radiation used in various manufacturing processes.

DESCRIPTION OF THE DRAWINGS

The device of the invention may be further understood by reference to the following drawings wherein:

In FIG. 1 an actinic radiation monitor is shown comprising a flat substrate 12 having deposited thereon a photochromic aziridine compound of Formula I in test zones 14. Associated with the aziridine compound is an oxygen barrier to prevent oxygen from contacting the aziridine compound. The surface of substrate 12 surrounding test zones 14 is colored with an appropriate color standard. The color of the standard is selected so as to match the color developed by the aziridine-oxygen barrier system from a known dosage of the radiation being monitored.

Figure 1:
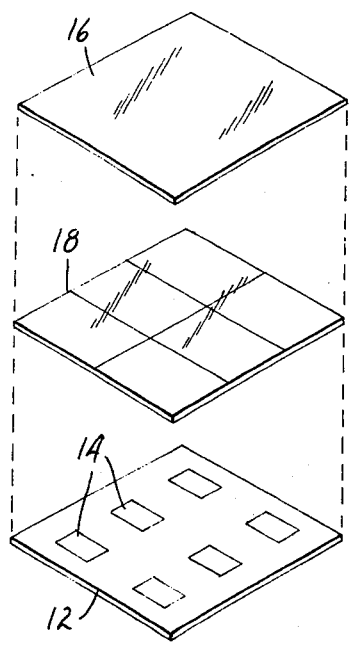
FIG. 1 is a schematic drawing showing the construction of a front side readout monitor.

Examples of suitable substrate material include cardboard, paper, metals, plastics, glass and ceramics. The photochromic aziridine compound may be laid down on the substrate, either from a solution in an organic solvent followed by drying and then overcoating with an oxygen barrier material, or as a dispersion in the oxygen barrier material. In any event, the aziridine compound must be in crystalline form. Silk screening, spraying, printing, painting or other coating techniques can be used. For ease in determining color match, it is preferred to utilize discrete geometric islands or test zones of the aziridine compound with the bulk of the substrate appropriately colored to a given intensity which represents the readout end-point. Differences in reflective optical density between the test zone and the background color standard as low as 0.03 can easily be discerned. It is obvious, however, that the color standard need not be actually attached to the monitor if it is otherwise available to the user for purposes of comparison.

The aziridine compound must be sealed in an oxygen barrier in order to prevent spontaneous thermal bleaching of the developed color. The aziridine compound may be deposited on the substrate and then overcoated with the oxygen barrier material. Alternatively, the aziridine compound may be dispersed in the oxygen barrier material prior to deposition on the substrate. This may be done, for example, by grinding or masticating the aziridine with a solution of the oxygen barrier material, coating the resulting dispersion on the substrate, and drying. It is preferred to combine these techniques and add additional coatings of the barrier material to prevent uneven oxygen penetration.

The aziridine compound must be in crystalline form in order to exhibit the necessary photochromic behavior. Thus, the oxygen barrier material or solvent associated therewith must not appreciably dissolve the aziridine compound when it is in its final radiation-sensitive construction. It is preferable to avoid the use of dispersing agents or diluents that render the barrier material less effective in excluding oxygen. The barrier material should be inert with respect to the aziridine compound and it must also be transparent or reasonably transmitting to the actinic radiation being monitored. The preferred oxygen barrier material is polyvinyl alcohol (PVA). An example and another suitable material is gelatin.

It is known that the oxygen permeability of polyvinyl alcohol increases with increasing relative humidity. For this reason, it is desirable that in a device used in high humidity, a moisture barrier be used in conjunction with the PVA. In the present invention, this moisture barrier can be supplied, for example, by completely sealing the entire monitor in a known moisture barrier filter such as a copolymer of vinylidene chloride and vinyl chloride ("Saran").

Treating the aziridine compound with an oxygen barrier material effectively eliminates the spontaneous thermal bleaching associated with the untreated compound, extending the lifetime of the normally fugitive blue form from a few hours to many months. However, the treatment does not affect the high sensitivity of the photochromic aziridine to ultraviolet radiation, nor does it eliminate the bleaching of the compound by visible light. Thus, in the absence of oxygen, the aziridine compound is a radiation integrator which can be bleached by a large exposure to visible light (in the absence of UV) and reused with little loss of accuracy.

The sensitivity of the aziridine compounds of Formula I to bleaching in the presence of oxygen varies with type of $R^1$ and $R^2$ groups present. A number of aziridine derivatives were synthesized using the method of Heine et al. and tested to determine their sensitivity to oxygen. Strips of filter paper were saturated with benzene solutions of the aziridines and dried. The resulting strips were irradiated with UV radiation to generate the blue form. One set of the irradiated strips was kept in a nitrogen atmosphere in the dark, and another set was kept in an oxygen atmosphere in the dark. Both sets were maintained at room temperature. The time required to bleach to one-half of the original optical density was estimated visually and is recorded in Table I below.

TABLE I

| Derivative | Time Required to Bleach to One-Half O.D. | |
|---|---|---|
| | $O_2$ Atm. | $N_2$ Atm. |
| $R^1 = R^2 = -CH_3$ | 40 minutes | >1 year |
| $R^1 + R^2 =$ cyclopentyl | 3 hours | >3 months |
| $R^1 + R^2 =$ cyclohexyl | 10 hours | ~2 months |
| $R^1 = -CH_3, R^2 = -C_6H_5$ | 10 minutes | ~3 months |
| $R^1 = H, R^2 = n-C_3H_7$ | 10 hours | 1 month |
| $R^1 = R^2 = -C_2H_5$ | 20 minutes | 3 days |
| $R^1 = CH_3, R^2 = -CH(CH_3)_2$ | 10 minutes | 3 weeks |
| $R^1 = H, R^2 = -C_6H_5$ | <10 minutes | 2 days |
| $R^1 = H, R^2 =$ o-methoxyphenyl | <10 minutes | 15 hours |

In FIG. 1, filter means 16 overlies substrate 12 and the aziridine-oxygen barrier layer. Filter 16 is a spectral response shaping filter. It screens out actinic radiation which will cause the aziridine compound to change color, but which is not the type being monitored. By reference to FIG. 3 it can be seen that the spectral response of a representative aziridine compound of Formula I is very broad. In a psoriasis treatment monitor, for example, radiation in only a portion of this spectrum (e.g., wavelengths of 320-390 nanometers), is being monitored. The spectral response shaping filter is designed to transmit only radiation of the type being monitored. This is accomplished by incorporating into the filter medium certain radiation-adsorbing compounds in a binder with or without a substrate. In some cases, a combination of binders and several discrete filter layers may be required in order to provide the proper spectral response. For example, a combination of Genacryl Yellow (C.I. #48055), phenyl salicylate and 2,4-dihydroxybenzophenone in a photocurable resin (described in U.S. Pat. No. 3,700,643) coated on Mylar Brand plastic film provides a single spectral response shaping filter for the psoriasis treatment monitor. However, for a sun exposure monitor, Alizarine Yellow (C.I. #14055) in a modified cellulose acetate mixture [cellulose acetate (100.0 parts), diethylphthalate (24.0 parts) and octadecyl 3-(3,5-di-tert-butyl-4-hydroxyphenyl proprionate (0.40 parts) hereinafter referred to as "mod. cell. acetate,"] and Setoflavin T (C.I. #49005) in polyvinyl alcohol, i.e., two separate layers, may be used in combination as the shaping filter.

In addition to a spectral response shaping filter, it is also desirable to have one or more attenuating filters 18 disposed between the photochromic layer and the source of actinic radiation, to reduce the amount of actinic radiation impinging on the photochromic layer. Without an attenuating filter, a complete color change may develop in a few seconds or less when a strong source of actinic radiation is present. The attenuating filter 18 screens out a portion of actinic radiation of the type being monitored, and allows the device to be used in monitoring high levels of radiation.

The attenuating filter is generally a combination of radiation absorbing substances in a binder which gives a flat response from about 300-400 nanometers. For example, a combination of Genacryl Yellow, Alizarine Yellow and 2,4-dihydroxybenzophenone in the photocurable resin gives an essentially flat response. The degree of attenuation depends on the concentration of radiation-absorbing substances in the filter. The attenuating filter may be a separate layer or combined with the spectral response shaping filter if the ingredients are compatible and a common binder can be used.

In some monitors, e.g., where multiple test zones are provided, it may be desirable to have a series of attenuating filters with progressively higher concentrations of radiation absorbing material. Each filter in the series is paired with corresponding test zones, thereby rendering the test zones progressively less sensitive to radiation. In this manner, a monitor can be fashioned which can be used by subjects with varying sensitivity to the radiation being monitored. For example, in a psoriasis treatment monitor having six test zones, a patient who is very radiation-sensitive may terminate exposure when the first or second test zone matches the color of the color standard. A more resistant patient may not terminate exposure until the fifth or sixth test zone has darkened to the color of the standard. Thus identical monitors can be used by subjects with varying sensitivities.

Although the attenuating filters are preferred in most monitors, the same effect can be achieved by varying the concentration of photochromic aziridine or by varying the thickness of the aziridine-oxygen barrier layer.

The monitor of FIG. 1 is well suited for psoriasis treatment. In the case of a sun exposure monitor where the monitor is exposed to a large amount of visible light, it is desirable to add a removable or retractable filter over the top of the monitor which is transparent or reasonably transmitting to erythemal radiation and filters out visible light. This prevents optical bleaching of the color developed by the aziridine compound. For example, a filter comprising the dye Basic Blue 7 (C.I. #42595) dissolved in mod. cell. acetate may be releasably secured to the top of the monitor. The filter remains in place during use, but is easily removed to visually read the color change of the photochromic layer. Alternatively, a back side read out device as shown in FIG. 2 may be used as a sun exposure monitor.

Figure 2:
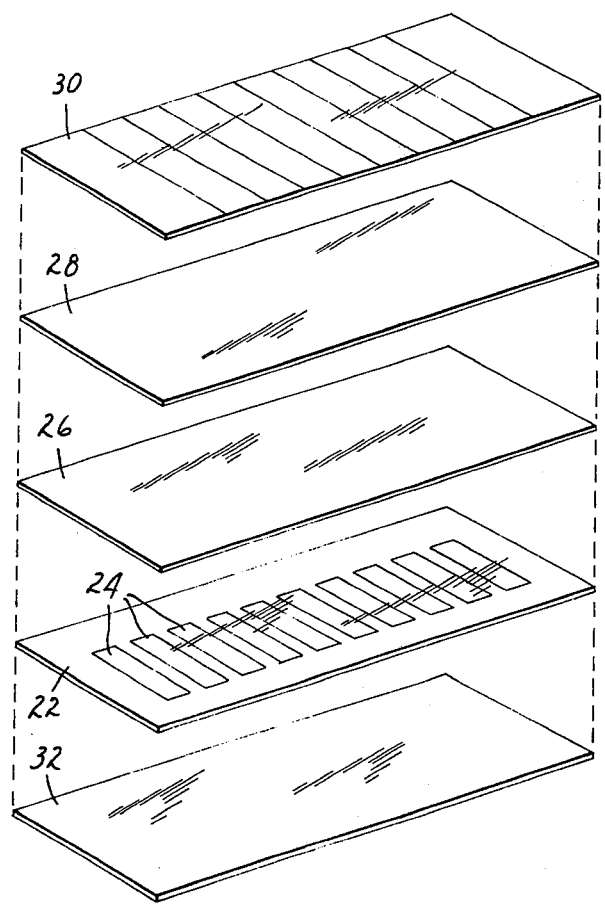
FIG. 2 is a schematic drawing showing the construction of a back side readout monitor.

FIG. 2 is an exploded schematic view of a back side read out monitor. The monitor comprises a substrate 22 which transmits the radiation being monitored having deposited on the underside thereof a photochromic aziridine compound of Formula I in test zones 24. Associated with the aziridine compound is an oxygen barrier such as polyvinyl alcohol. The portion of substrate 22 surrounding test zones 24 provides a color standard with which to compare the color developed by the aziridine compound to determine an "end point." Overlying substrate 22 is filter 26 which is opaque to visible light and reasonably transmitting to ultraviolet light. An example of such a filter is Basic Blue 7 in mod. cell. acetate. Overlying filter 26 is spectral response shaping filter 28. Filter 28 screens actinic radiation outside the range being monitored. For example, in a sun exposure monitor, filter 28 should screen out radiation having wavelengths of about 330 nanometers to 450 nanometers and transmit radiation in the range of about 280 nanometers to 320 nanometers. Attenuating filter 30 is disposed over shaping filter 28. Attenuating filter 30 may be a series of discrete filters with varying concentrations of ultraviolet light-absorbing compounds to produce a stepwise response by test zones 24. Again, the shaping filter 28 and attenuating filter 30 may be combined in some cases into a single layer. On the back side of substrate 22 is layer 32 which filters out ultraviolet radiation that would cause the aziridine compound to change color, but transmits visible light so that the color change of the photochromic layer can be read visually from this side of the monitor.

Figure 3:
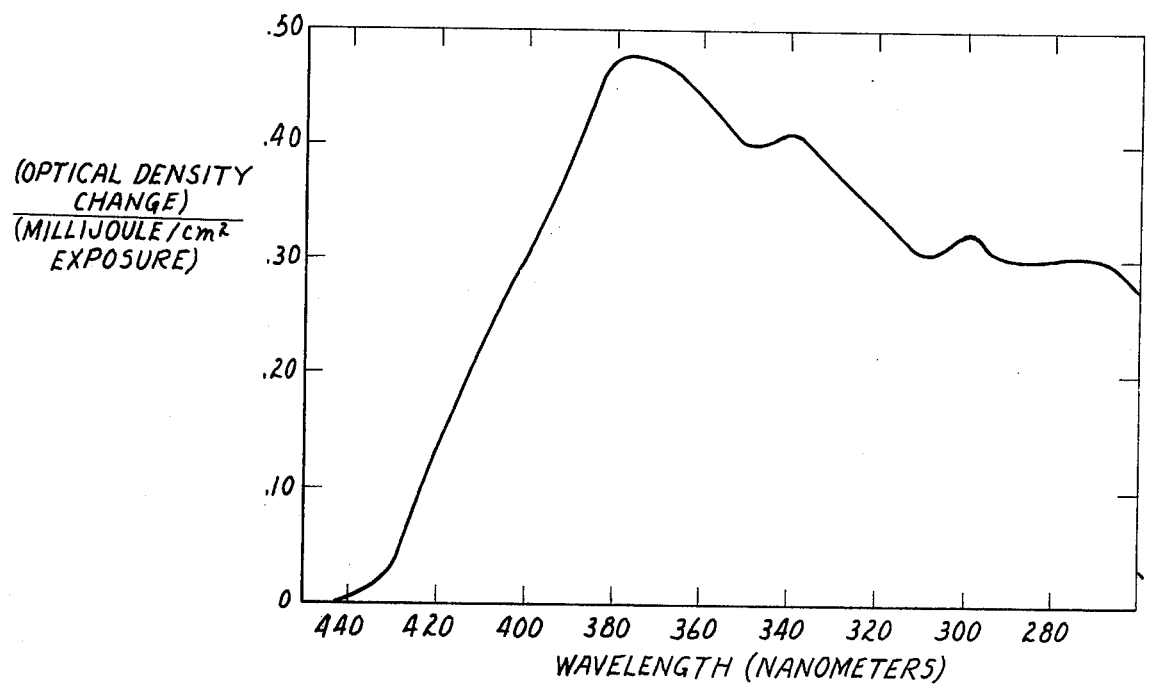
FIG. 3 is a curve of the spectral response of a representative aziridine compound in an oxygen barrier (polyvinyl alcohol)

The spectral response curve of the $R^1 = R^2 = CH_3$ aziridine derivative of Formula I in polyvinyl alcohol is shown in FIG. 3. Considerable sensitivity in the visible and far ultraviolet region indicates the necessity for filtering certain non-essential radiation. However, with a proper spectral response shaping filter, the only radiation the aziridine will "see" is the radiation that is active in the system involved.

Figure 4:
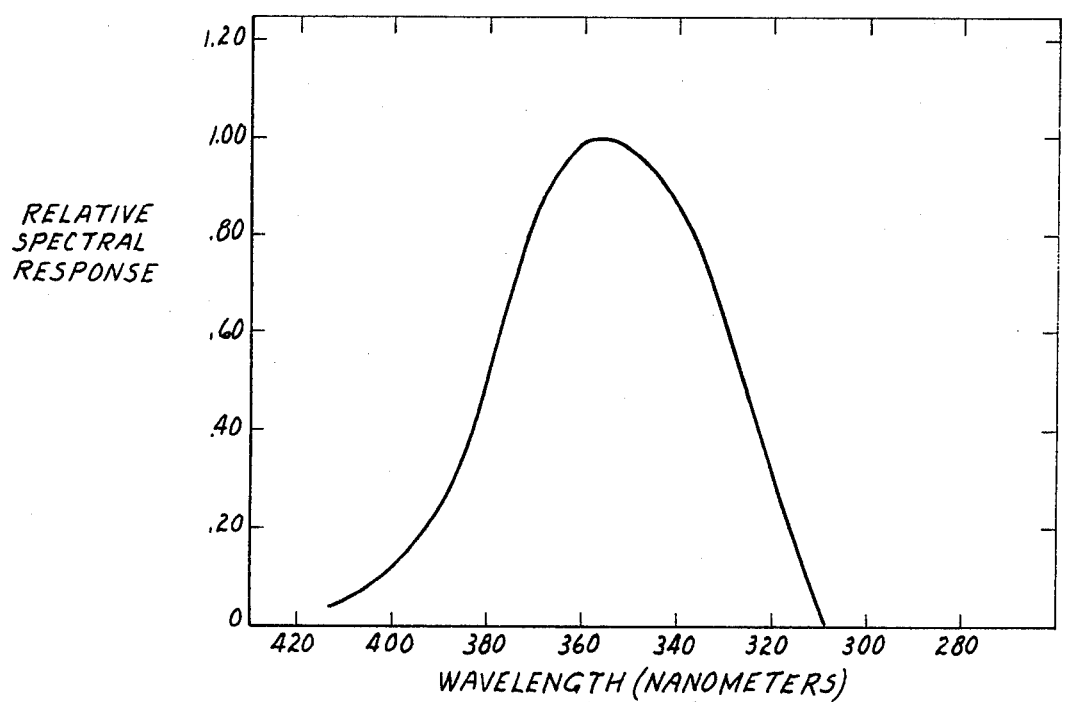
FIG. 4 is a curve showing the spectral response of a typical psoriasis treatment monitor.
Figure 5:
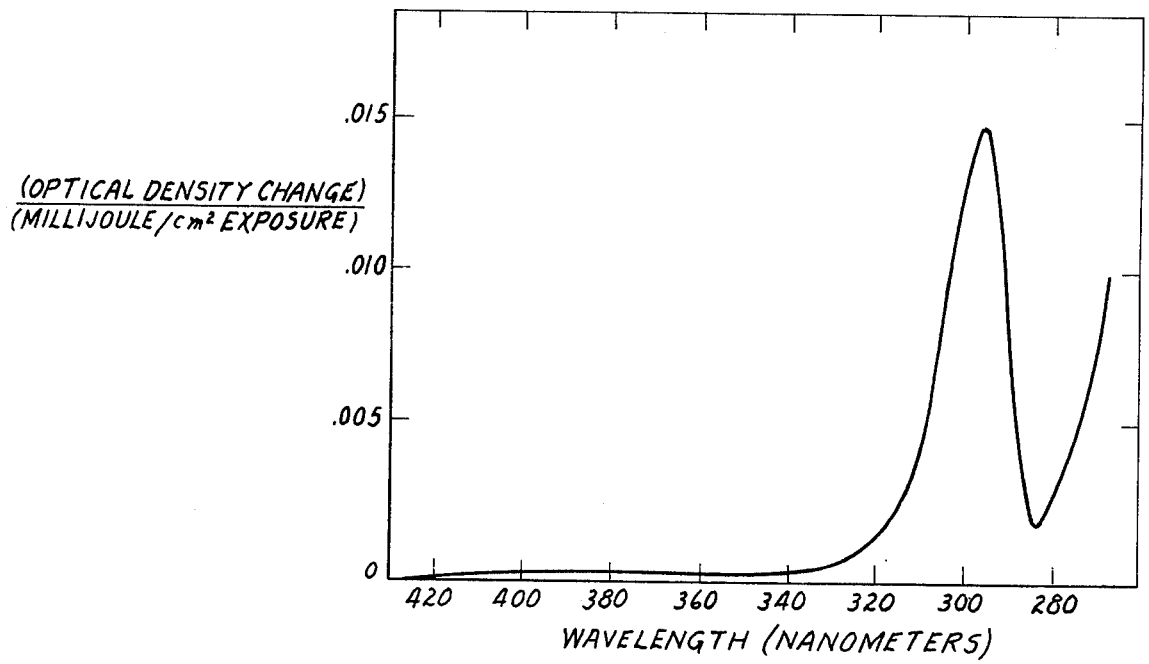
FIG. 5 has a curve showing the spectral response of the typical sun exposure monitor.

FIG. 4 shows the spectral response of a typical monitor useful in the psoriasis treatment procedure. This spectral response is obtained by providing the appropriate shaping filter or filters to screen out radiation outside the desired range. FIG. 5 shows the spectral response of a typical sun exposure monitor.

The product of spectral response of aziridine-PVA (at a given wavelength, λ) and the transmittance of the filter system (at a given wavelength, λ) gives the spectral response of the device. Mathematically, $$[S_{device}]_\lambda = [S_{aziridine-PVA}]_\lambda \cdot [T_{filter}]_\lambda$$

where
$S_{device}$ is the spectral response of the device
$S_{aziridine-PVA}$ is the spectral response of the aziridine-PVA dispersion
$T_{filter}$ is transmittance of the filter system
λ is the wavelength at which measurements were made It is apparent from FIG. 3 that the filter system can be modified to adjust the monitor to a variety of radiation exposure problems.

The monitor of the invention is further illustrated by the following nonlimiting examples.

EXAMPLE 1

Psoriasis Treatment Monitor (Front Side Readout)

The aziridine compound, 2,2'-dimethyl-6(p-nitrophenyl)-4-phenyl-1,3-diazabicyclo[3.1.0]hex-3-ene (0.25 g), was ground to a fine particle size in a mortar and pestle. Aqueous polyvinyl alcohol (PVA) solution (3 g of 4% solution) was added to the aziridine compound and the mixture was ground for a few minutes to achieve a uniform dispersion. The dispersion was applied by brush to bond paper and dried with a heat gun. The entire substrate was then dipped in an aqueous 4% PVA solution and dried with a heat gun. Dipping and drying were repeated three more times to completely seal the aziridine compound from oxygen.

Patches of the aziridine coated substrate (about 0.25 cm$^2$) were attached to a color standard sheet. The color standard sheet was bond paper coated with blue Benjamin Moore Formulation 9–31 Flat Latex paint. This paint was selected because of the visual match between it and the colored form of the aziridine dispersion at a reflective optical density of 0.84 when viewed through the filter system (described below). Five patches of aziridine coated substrate were attached to strips of the color standard sheet about 1.5 cm × 7.5 cm so that the patches were completely surrounded by the colored background. The entire strip was then coated with a 4% aqueous solution of PVA.

The attenuating filters were prepared by first making a master mix and then successively diluting it to achieve various concentrations. The master mix was prepared as follows: Hylene WS (53.5 g — DuPont 4,4'-methylenebiscyclohexylisocyanate) was charged to a 250 ml three-neck flask and stirred and heated to 50° C. Polycaprolactone polyol (83.0 g — molecular weight about 530) was added and the temperature rose to 84° C. After 2 hours of stirring, the temperature had decreased to 65° C. Dibutyltin dilaurate (0.24 g) was then added. Hydroxyethyl methacrylate (HEMA, 37.4 g) was slowly added to the stirred mixture and allowed to react for about 45 minutes. The resulting syrupy mixture was designated Oligomer "A". Oligomer "A" (5.05 g) was mixed with 5.05 g of V-Pyrol® monomer (N-vinyl-2-pyrrolidone from GAF Corp.). To this mixture, anisoin ethyl ether (0.5 g) and α,α-diethoxyacetophenone (0.1 g) were added. To the resulting solution, Genacryl Yellow 3G (C.I. #48055, 2.0 g), 2,4-dihydroxybenzophenone (0.424 L g) and Alizarine Yellow 5GS (C.I. #14055, 0.0386 g) were added sequentially and stirred until dissolved. This solution was added to a mixture of Oligomer "A" (43.3 g), HEMA (43.3 g) and α,α-diethoxyacetophenone (0.866 g) to form the master mix. The master mix was diluted with various amounts of a diluent made of 1:1 Oligomer "A":HEMA + 1 wt% α,α-diethoxyacetophenone as shown in Table II.

TABLE II

| Sample | Master Mix (g) | Diluent (g) |
|---|---|---|
| 1 | 9.9997 | 0 |
| 2 | 10.0002 | 0.5798 |
| 3 | 7.9999 | 1.2223 |
| 4 | 7.0002 | 1.7830 |
| 5 | 5.9999 | 2.8716 |

Each of these solutions was coated onto Mylar Brand Plastic Film with a #44 Meyer bar and exposed under a nitrogen atmosphere to a bank of Sylvania F15T 8/BL lamps for 2.5 minutes on the coated side, 10 minutes on the back side, and then an additional 5 minutes on the coated side. The resulting cured films provide a relatively flat spectral response to near UV radiation.

The cured films are easily removed from the Mylar Brand plastic film and cut into the appropriate size to fit over the photochromic aziridine patches. The most concentrated mixture film is conveniently attached to the patch at one end of the substrate, with a systematic decrease in concentration over the other patches.

The spectral response shaping filter was prepared by dissolving the following ingredients in 48.5 g of a 1:1 mixture of Oligomer "A" and HEMA:

0.750 g Genacryl Yellow 3G (C.I. #48055);
0.0782 g dihydroxybenzophenone;
0.213 g phenylsalicylate;
0.252 g anisoin ethyl ether; and
0.260 g α,α-diethoxyacetophenone.

The resulting solution was coated on Mylar with a #44 Meyer bar and cured in a nitrogen atmosphere with a bank of Sylvania F15T 8/BL lamps. The coated side was exposed for ten minutes and the backside for five minutes. The resulting film was peeled from the Mylar Brand plastic film and was 0.068 mm thick. A portion of this film 1.5 cm × 7.5 cm was attached to the attenuating filters. The entire assembly was covered by a layer of Mylar Brand plastic film to form a monitor. The monitor was exposed to a pair of Sylvania FR 40 Bl-235 lamps. These lamps have an emission spectrum similar to the lamps used in treating psoriasis. As the monitor was exposed to the radiation, the photochromic aziridine changed to a blue color. The patch under the attenuating filter 5 first matched the color of the color standard followed by 4 through 1 as the length of time of exposure increased. By the time that the patch under filter 1 matched the color of the standard, the other patches were darkened so that it was very easy to visually determine that their "end-points" had been passed.

At the point where the color of the photochromic aziridine patch matched the color standard, the reflective optical density (hereinafter referred to as "optical density") was 0.88 through the monitor's filters as measured by a MacBeth RD-519 Densitometer with cyan filter.

A monitor was exposed to the Sylvania FR 40 BL-235 lamps until the color of all patches had passed the "end-point." The optical density of each patch was determined and the monitor was then placed in the dark for 72 hours. At the end of this time, the optical density was measured again. The data is recorded in Table III. There was little change in optical density following 72 hours in the dark. The monitor was then exposed to a yellow G.E. "Bug Lite" at a distance of 15 cm for two hours. The optical density was determined. The results (also shown in Table III) indicate that the bleaching under visible radiation is substantial, and that the monitors may be reused.

TABLE III

| | Optical Density | | | | |
|---|---|---|---|---|---|
| Sample | 1 | 2 | 3 | 4 | 5 |
| Immediately after exposure to UV | 1.00 | 1.12 | 1.34 | 1.32 | 1.39 |
| After 72 hours in dark | 0.96 | 1.09 | 1.29 | 1.28 | 1.39 |
| After exposure to visible light | 0.26 | 0.26 | 0.26 | 0.26 | 0.26 |

Comparison of the spectral response of this device and the physiological response of human skin following ingestion of 8-methoxypsoralen indicates that it would be a superior monitor for determining the radiation exposure in psoriasis treatment.

EXAMPLE 2

The aziridine compound, 2,2'-dimethyl-6(p-nitrophenyl)-4-phenyl-1,3-diazabicyclo[3.1.0]hex-3-ene was dispersed in an aqueous polyvinyl alcohol solution. The solution was applied to white cardboard and completely sealed in PVA as described in Example 1.

The monitor was then prepared as follows:

The entire light sensitive substrate was covered with masking tape. The masking tape was cut and removed in areas where the color standard is to be applied. The entire surface was covered with Benjamin Moore 9-31 Flat Latex paint. The masking tape (in areas of light-sensitive patches) was then removed.

The entire substrate was then dip-coated in 4% PVA and dried (repeated three times).

Filters (combining the spectral response shaping filter and the attenuating filter into one) to be placed over the individual patches were prepared in the following manner.

A master dye mixture was prepared by adding the following ingredients to 1324 g of 20.5% mod. cell. acetate in acetone solution:

14.8391 g Genacryl Yellow (Berncolors, Inc. - Bernacryl Yellow, 4G);

1.4298 g Alizarine Yellow (Berncolors, Inc. -Bernachrome Yellow 6G);

2.3421 g dihydroxybenzophenone; and 2.0992 g phenyl salicylate.

The mixture was warmed and stirred to dissolve the dyes and then passed through a pressure filter.

A series of dilutions of this master mixture was made by adding various amounts of 20.5% mod. cell. acetate-/acetone solution. Samples of these solutions were knife-coated at wet thicknesses of 3.65 mm and then air dried in an oven at 80° C. (0.0457 mm dry). Samples were selected that gave representative endpoints of each film when placed over the aziridine dispersion and exposed with the FR 40 BL-235 lamps. The dilutions used in this example are given below.

| Sample # | Amount of Master Mix (g) | Amount of 20.5% Mod. Cell. Acetate in Acetone (g) |
|---|---|---|
| 1 | 100 | 0 |
| 2 | 93.5 | 8.7 |
| 3 | 85.0 | 15.0 |
| 4 | 76.0 | 24.0 |
| 5 | 85.0 | 33.0 |

Samples of these films were cut to size and fixed to the aziridine patches with Dow Corning SILASTIC 732 RTV adhesive. A layer of 2 mil Mylar Brand plastic film was then glued over all five filters with the SILASTIC adhesive, and the entire assembly was allowed to cure under pressure for 24 hours.

The monitor was exposed to a pair of FR 40 BL-235 lamps at the rate of 2.08 milliwatts/cm$^2$ (measured with a Gamma Scientific 820A Photometer) until each of the endpoints had been reached. The sample was then optically bleached with a GE "Bug Lite." This cycle was repeated two more times.

On the fourth cycle, the optical density of each of the patches was measured periodically (through the filters) with an RD-100 densitometer. The sample was subsequently bleached optically and a fifth cycle of UV exposure given. At the end of the fifth exposure, the sample was placed in the dark and left for 69 hours at room temperature. Optical density readings were then taken. These data are summarized below.

The underlined readings, in each sample, were the previously judged visual "endpoints." Thus, in these 10 determinations the visual endpoints varied with optical density between 0.89 and 0.92 (< 3%), and the extent of bleaching in the dark was minimal.

| Exposure (J/cm$^2$) | 4th Exposure Cycle Optical Density of Sample # | | | | |
|---|---|---|---|---|---|
| | 1 | 2 | 3 | 4 | 5 |
| 0 | .28 | .27 | .30 | .28 | .26 |
| .196 | .45 | .39 | .36 | .32 | .31 |
| .595 | .62 | .56 | .46 | .40 | .36 |
| 1.28 | .83 | .73 | .55 | .48 | .42 |
| 1.58 | .92 | .80 | .60 | .52 | .46 |
| 2.18 | | .92 | .68 | .62 | .52 |
| 4.05 | | | .85 | .76 | .67 |
| 4.75 | | | .91 | .81 | .70 |
| 5.74 | | | | .87 | .76 |
| 6.72 | | | | .89 | .77 |
| 9.87 | | | | | .90 |

| Exposure (J/cm$^2$) | 5th Exposure Cycle Optical Density of Sample # | | | | |
|---|---|---|---|---|---|
| | 1 | 2 | 3 | 4 | 5 |
| 0 | .29 | .28 | .31 | .28 | .28 |
| .196 | .44 | .37 | .34 | .34 | .29 |
| .595 | .62 | .53 | .42 | .41 | .34 |
| 1.49 | .91 | .78 | .58 | .52 | .46 |
| 2.18 | | .92 | .70 | .61 | .52 |
| 3.96 | | | .88 | .78 | .68 |
| 4.45 | | | .89 | .79 | .68 |
| 5.75 | | | | .86 | .73 |
| 6.72 | | | | .92 | .78 |
| 8.90 | | | | | .85 |
| 10.6 | | | | | .90 |

| Optical Density After Standing in Dark 69 Hours | | | | |
|---|---|---|---|---|
| .86 | .88 | .88 | .82 | .86 |

EXAMPLE 3

Psoriasis Treatment Monitor (Back Side Readout)

The radiation sensitive substrate was prepared as shown schematically in FIG. 2 by coating an aziridine-PVA dispersion to a thickness of approximately 0.025 mm on phenylterminated polycarbodiimide-primed polyester and subsequently coating with PVA as described in Example 1. A color standard background was prepared by coating primed polyester with the latex paint described in Example 1. Ten holes (about 0.25 cm$^2$) were punched in this reference strip, and transparent doublecoated pressure sensitive adhesive tape was attached to the uncoated side over the holes. Patches of the light sensitive substrate were then pressed into the holes in the reference strip and held in position with the pressure sensitive adhesive. A strip of tracing paper (Crane - 100% cotton from American Pad and Paper Co.) (1.5 cm × 7.5 cm) was placed over the painted surface.

The filter system for the exposure side consisted of a layer of the spectral response shaping filter of Example 1, and a neutral density step wedge filter (Stouffer #95). The neutral density step wedge filter was placed over the spectral response shaping filter with each step covering a different light sensitive patch. The readout side was covered with visible transmitting UV-absorbing filters made up of the spectral response shaping filter plus a filter of the cured master mix of Example 1 and held in place by the double-coated pressure sensitive adhesive tape.

The assembled monitor was exposed for 16 minutes to the FR 40 BL-235 lamps of Example 1 at the rate of 1.8 × 10$^{-3}$ watts/cm$^2$ and the difference in the color intensity of the various segments could be easily distinguished visually. Reflectance O.D. measurements were subsequently made through the filters of the readout side using a MacBeth RD-519 densitometer with a cyan filter. The results are shown in Table IV.

TABLE IV

| Segment | Optical Density |
|---|---|
| 1 | 1.10 |
| 2 | 1.12 |
| 3 | 1.02 |
| 4 | 1.00 |
| 5 | .88 |
| 6 | .82 |
| 7 | .79 |
| 8 | .74 |
| 9 | .69 |
| 10 | .64 |

TABLE IV-continued

| Segment | Optical Density |
|---|---|
| Background | 1.03 |

EXAMPLE 4

Sun Exposure Monitor (Front Side Readout)

The Yellow dye, Setoflavin T (C.I. #49005, 0.0225 g), was dissolved in 7 cc of a 4% aqueous PVA solution. This dyed PVA solution was then mixed with the aziridine compound (0.25 g) to make the light-sensitive substrate as described in Example 1. The aziridine-PVA color standard configuration shown in FIG. 1 was used.

Alizarine Yellow (C.I. #14055, 0.0345 g) was dissolved in one ml of 1:1 ethanol:acetone. This solution was mixed with 2.83 g of 39% mod. cell. acetate in acetone and then coated onto a Mylar Brand plastic film web using a #44 Meyer Bar (dried film thickness - 0.01 mm).

Films of the Alizarine Yellow/mod. cell. acetate were then laid over patches of the Setoflavin-aziridine substrates. The first patch was covered by one film, and the second by two. A CS-7-54 (Corning Glass Works - Corning Glass #9863) UV-transmitting, visible-blocking filter was placed over all of the segments.

This assembly was exposed outside to full (Minnesota winter) sunlight. After 25 minutes exposure, the light sensitive patch under a single film was considerably darker, but only slightly darker under two films. Reflectance O.D. readings were made through the Alizarine Yellow (C.I. #14055)-mod. cell. acetate film using a MacBeth RD-519 densitometer (cyan filter). The data is recorded in Table V.

TABLE V

| | O.D. | |
|---|---|---|
| Time | 1 Film | 2 Films |
| Start | .23 | .23 |
| Expose 2:10–2:35 p.m. | 1.40 | .29 |
| Expose 2:50–4:20 p.m. | 1.51 | .54 |

Transmittance measurements as a function of wavelength were made of a combination of two layers of the 3.1% Alizarine Yellow-mod. cell. acetate and a 0.015 mm film of 3.2% Setoflavin/PVA. These transmittance values and the aziridine-PVA response values were multiplied to get the approximate device spectral response shown in FIG. 5.

EXAMPLE 5

Three dispersions of aziridine compound in PVA were prepared as in Example 1, each having different aziridine/PVA ratio. These were coated to approximately 0.05 mm thickness onto cardboard. A spectral response shaping filter (Example 1) was placed over samples of each of the dispersions. They were then exposed to the blacklights of Example 1 and optical density readings were taken. The readings (Table VI) illustrate that it is posssible to obtain a spread of endpoints by using a common filter, but different loadings of aziridine in the light sensitive substrate, and these differences can be observed visually.

TABLE VI

| Weight | | Weight Ratio Aziridine/- | Optical Density Exposure | | |
|---|---|---|---|---|---|
| Aziridine | 4% PVA | PVA | 0 | 10 mj/cm$^2$ | 40 mj/cm$^2$ |
| .0186 g | .178 g | 2.6 | .12 | .26 | .88 |
| .0070 g | .178 g | .98 | .12 | .22 | .59 |
| .0018 g | .178 g | .25 | .12 | .15 | .27 |

In carrying out the above measurements, the spectral response shaping filter was removed prior to determining the optical density.

EXAMPLE 6

Plant Lighting Indicator for Red Light Response (Bleaching Mode)

Filter paper was dipped in a saturated benzene solution of the $R^1 = R^2 = CH_3$ derivative and the solvent evaporated. This strip was coated with 4% PVA and dried with a heat gun. The PVA coating was repeated three more times. The sample was irradiated to an optical density of 0.70 (RD 100 densitometer).

Strips of 3M brand infrared transparency film Type #577 were stacked to various thicknesses over the irradiated aziridine to make a step-wedge attenuating filter for red light. A CS-3-69 UV cut-off, visible transmitting filter was placed over this wedge. The entire assembly was taped to a cardboard backing.

One of these indicators was placed in a window with northern exposure and one with a southern exposure (both inclined 45°). They were exposed from sunrise to sunset on a cloudy-bright January day. There was significantly more bleaching in the sample given southern exposure.

The experiment was repeated on a totally cloudy January day. Both samples showed equal bleaching, but considerably less bleaching than that found in the monitors exposed on the cloudy-bright day.

The experiment was repeated on a totally sunny day. For the sample given a southern exposure, complete bleaching occurred at all positions having up to 10 layers of the blue transparency material over them. For the sample left in the northern exposure, only a trace of bleaching occurred under the area with 4 layers. No noticeable bleaching occurred in areas covered with more than 4 layers.

EXAMPLE 7

Plant Lighting Indicator for Blue Light Response

A substrate was prepared as described in Example 2. Alizarine Yellow (4.0g of Bernchrome Yellow) and 4.0 g of tetrahydroxybenzophenone were dissolved in a solution of 14.5% mod. cell. acetate in acetone. This served as the master solution used to make the combined spectral shaping and attenuating filters. This solution was diluted with 14.5% mod. cell. acetate to make representative samples. These samples were coated to 0.38 mm wet (0.056 mm dry) by a knife coating and dried two hours in an 80° C. oven. From these films, two samples were selected.

Basic Blue 7 (C.I. #42595, 0.362g) was dissolved in 159.4 g of 24.2% mod. cell. acetate in acetone and coated with a knife coater to 0.305 mm wet, 0.046 mm dry). This filter, which is to be removed during readout, attenuates visible light in the red region of the spectrum where the aziridine is most easily optically bleached. (It is, however, essentially transmitting in the near-UV and far visible region).

Samples of the Alizarine Yellow/tetrahydroxybenzophenone in mod. cell. acetate filters were placed over the indicators and then a layer of 0.05 mm Mylar Brand plastic film placed over that. A layer of the Basic Blue 7 film was laid temporarily over the entire assembly. These indicators were then placed 7 cm from a pair of GE #40CW Cool White Fluorescent lamps (3.24 milliwatts/cm$^2$ total output at sample plane). Reflective optical density readings of the aziridine/PVA layer were taken periodically (through the filters) with a MacBeth RD-100 densitometer (yellow filter position). These readings are given in Table VII.

TABLE VII

| Sample # | # Grams Master Mixture | # Grams 14.5% Mod. Cell. Acetate/Acetone | Optical Density After Total Exposures of (Joules/cm$^2$) | | | |
|---|---|---|---|---|---|---|
| | | | 0 | 9.72 | 23.3 | 65.2 |
| 1 | 100 | 0 | .44 | .82 | 1.00 | 1.15 |
| 2 | 80 | 20 | .52 | .96 | 1.12 | 1.32 |

The Basic Blue 7 Filter was removed and the sample was bleached with a GE "Bug Lite."

EXAMPLE 8

Electron Beam Radiation Monitor

The aziridine, 2,2'-dimethyl-6(p-nitrophenyl)-4-phenyl-1,3-diazabicyclo[3.1.0]hex-3-ene (0.25 gm), was ground to a fine particle size in a mortar and pestle. Aqueous polyvinyl alcohol (PVA) solution (3 gm of 4% solution) was added to the aziridine and the mixture was then ground for a few minutes to achieve a uniform dispersion. The dispersion was applied by brush to bond paper and dried with a heat gun. The entire substrate was then dipped in an aqueous 4% PVA solution and dried with a heat gun. Dipping and drying was repeated three more times to completely seal the aziridine from air. Patches of this material were attached to the comparison sheet in the manner of Example 1 and the entire substrate was dip-coated in 4% PVA solution and dried. The entire monitor substrate was covered with a single layer of the UV-attenuating, visible transmitting film prepared for the psoriasis treatment monitor of Example 1, Sample 1 (0.068 mm) to prevent coloraton by room light. Different thicknesses of Mylar Brand plastic film were then stacked over each of the light sensitive patches to provide step-wise attenuation of the electron beam.

This assembly was fixed to a cardboard backing and passed through the purged exposure chamber of an Energy Sciences Electrocurtain Systems high energy electron beam radiation curing unit (accelerating potential - 175 Kev, beam current - 4.32 × 10$^{-6}$ amps/cm$^2$, 1.11 second exposure (0.84 Joules/cm$^2$). After exposure, reflective optical densities were measured for each of the patches of the monitor (through the filters) using an RD-519 densitometer (blue filter position).

The samples was then re-exposed under the same conditions (cumulative electron beam exposure - 1.68 Joules/cm$^2$). The effects of these exposures on the optical densities of the various segments is shown in Table VIII.

TABLE VIII

| Segment | Total Thickness of Beam Attenuating Layers (UV-Cut off and Mylar Filter) | O.D. Before Exposure | O.D. After Electron Beam Exposures of | |
|---|---|---|---|---|
| | | | .84 Joules/cm$^2$ | 1.68 Joules/cm$^2$ |
| 1 | .094 mm | .18 | 1.28 | — |
| 2 | .129 mm | .22 | 1.03 | 1.23 |
| 3 | .170 mm | .24 | .34 | .40 |
| 4 | .221 mm | .34 | .34 | .33 |
| 5 | .246 mm | .38 | .38 | .37 |
| 6 | .272 mm | .36 | .36 | .36 |
| 7 | .297 mm | .39 | .42 | .42 |
| 8 | .322 mm | .35 | .39 | .36 |

This sample was optically bleached with a GE "Bug Lite" and re-imaged. The sample showed little or no loss of sensitivity.

In addition to the above application of the monitor as as indicator of cumulative exposure, the monitor substrate could be used as a beam penetration indicator.

What is claimed is:

1. A integrating, reusable device for monitoring actinic radiation of a preselected character comprising: a substrate having deposited thereon at least one photochromic aziridine compound of the formula

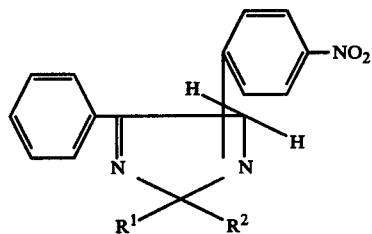

wherein R$^1$ and R$^2$ taken separately are hydrogen, alkyl having one to six carbon atoms inclusive, phenyl or ortho or para lower alkyl or lower alkoxy substituted phenyl, or R$^1$ and R$^2$ taken together are alkylene having 4 to 7 carbon atoms inclusive;
 an oxygen barrier associated with said aziridine compound to substantially prevent contact of said aziridine compound with oxygen;
 filter means disposed between said aziridine compound and the source of actinic radiation to filter out actinic radiation other than that of the preselected character; and
 at least one color standard with which to compare the color change of said aziridine compound caused by exposure to the actinic radiation.

2. A device according to claim 1 further comprising a removable visible-light filter overlying said aziridine compound.

3. A device according to claim 1 further comprising means for attenuating the amount of actinic radiation impinging on said aziridine compound.

4. A device according to claim 3 further comprising multiple discrete test zones of said aziridine compound deposited on said substrate.

5. A device according to claim 4 wherein said test zones are made progressively less sensitive to the radiation being monitored by having associated therewith a series of attenuating filters which progressively filter out more of the radiation being monitored.

6. A device according to claim 4 wherein said test zones are made progressively less sensitive to the radiation being monitored by varying the concentration of aziridine compound in each test zone.

7. A device according to claim 1 wherein $R^1$ and $R^2$ are methyl.

8. A device according to claim 1 where $R^1$ and $R^2$ taken together are cyclopentyl or cyclohexyl.

9. A device according to claim 1 wherein the oxygen barrier is polyvinyl alcohol.

10. A device according to claim 9 further comprising a humidity barrier overlying said aziridine compound and said oxygen barrier.

11. An integrating reusable device for monitoring exposure to actinic radiation of a preselected character comprising:
   a substrate which transmits the radiation being monitored having deposited on the underside thereof at least one photochromic aziridine compound of the formula

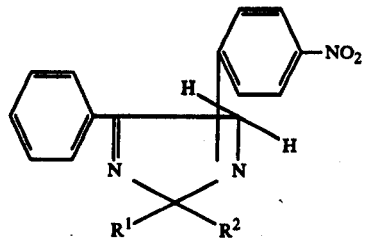

wherein $R^1$ and $R^2$ taken separately are hydrogen, alkyl having one to six carbon atoms inclusive, phenyl or ortho or para lower alkyl or lower alkoxy substituted phenyl, or $R^1$ and $R^2$ taken together are alkylene having 4 to 7 carbon atoms inclusive;
   an oxygen barrier associated with said aziridine compound to substantially prevent contact of said aziridine compound with oxygen;
   filter means disposed between said aziridine compound and the source of actinic radiation to filter out actinic radiation other than that of the preselected character;
   at least one color standard with which to compare the color change of said aziridine compound caused by exposure to the actinic radiation; and
   an actinic radiation filter overlying the aziridine compound on the under side of said substrate which transmits visible light.

* * * * *